United States Patent [19]
Falk et al.

[11] Patent Number: 5,368,274
[45] Date of Patent: Nov. 29, 1994

[54] LOW POWER ELECTROMAGNETIC VALVE

[75] Inventors: Theodore J. Falk, Clarence; W. Richard Brown, Clarence Center; Lawrence E. Morris, Bowmansville; Norbert W. Franz, Jr., Clarence, all of N.Y.

[73] Assignee: Wilson Greatbatch Ltd., Clarence, N.Y.

[21] Appl. No.: 946,392

[22] Filed: Sep. 17, 1992

[51] Int. Cl.⁵ ............................................. F16K 31/04
[52] U.S. Cl. ...................... 251/129.16; 251/129.17
[58] Field of Search ...................... 251/129.16, 129.17, 251/129.18, 129.21; 335/260

[56]                References Cited
        U.S. PATENT DOCUMENTS

| | | | |
|---|---|---|---|
| 2,697,581 | 12/1954 | Ray | 251/129.17 |
| 3,406,715 | 10/1968 | Hruby, Jr. | 137/550 |
| 4,196,751 | 4/1980 | Fischer | 251/129.16 |
| 4,390,130 | 6/1983 | Linssen | 251/129.16 |
| 4,541,429 | 9/1985 | Prosl | 251/129.21 |
| 4,621,660 | 11/1986 | Klocke | 251/129.09 |
| 4,714,234 | 12/1987 | Falk | 251/129.17 |
| 4,858,956 | 8/1989 | Taxon | 251/129.18 |
| 4,936,337 | 5/1990 | DuHack | 251/129.15 |

*Primary Examiner*—Robert G. Nilson
*Attorney, Agent, or Firm*—Hodgson, Russ, Andrews, Woods & Goodyear

[57]                ABSTRACT

An electromagnetic valve comprising a housing having a fluid containing region and first and second ports in communication with the region, an electromagnet carried by the housing located external to the fluid containing region, and a thin diaphragm of fluid impermeable material which hermetically isolates the electromagnet from the fluid containing region. An armature is movably positioned in the region and has a pole portion located for magnetic attraction by the electromagnet and has a plunger portion provided with a valve formation for opening and closing one of the ports to place both ports in fluid communication through the fluid containing region of the housing and to block fluid communication between the ports. The armature is moved from a rest position through a forward stroke when attracted by the electromagnet to change the control state of the valve, and the armature is moved by a biasing spring in an opposite direction through a return stroke back to the rest position. The armature pole portion is of a material selected to achieve a desirable balance between fluid compatibility and magnetic properties for rapid and effective valve operation. Passages in the barrier and the armature pole portion allow the rapid valve movement and accommodate bubbles in the fluid, the armature is provided with structure for effectively guiding the same, and a valve seat structure resists fluid leaks.

28 Claims, 2 Drawing Sheets

LOW POWER ELECTROMAGNETIC VALVE

BACKGROUND OF THE INVENTION

This invention relates to the art of electromagnetically-operated fluid valves, and more particularly to a new and improved electromagnetic valve which operates at extremely low power for use in implantable fluid delivery systems.

The principal requirements for a valve in such fluid delivery systems are low power drain, since the valve must be driven by an implanted battery, and compatibility with the drug being handled. Additional considerations include optimum magnetic characteristics of certain valve components, improved reliability and reduced cost. It would, therefore, be highly desirable to provide an electromagnetically-operated valve which is safe, reliable, light in weight, small in size, which operates without excessive demand on the available energy supply and which is compatible with drugs or similar liquids being handled. It also would be advantageous to provide such a valve which achieves a desirable balance between drug compatibility of component material and electromagnetic properties of that material, which insures rapid and effective closing of the valve, which accommodates bubbles in the fluid, which is resistant to fluid leaks, which provides effective guiding of moving valve components and which is relatively easy to assemble.

SUMMARY OF THE INVENTION

It is, therefore, a primary object of this invention to provide a new and improved electromagnetically-operated valve for use in implantable fluid delivery systems.

It is a more particular object of this invention to provide such a valve which operates at extremely low power levels.

It is a further object of this invention to provide such a valve which is compatible with drugs and similar liquids being handled.

It is a further object of this invention to provide such a valve which achieves a desirable balance between fluid compatibility and electromagnetic properties of material of valve components.

It is a more particular object of this invention to provide such a valve which features rapid opening and closing, resists fluid leaks, accommodates bubbles in the fluid and provides effective guiding of moving valve components.

It is a further object of this invention to provide such a valve which is small in size, light in weight, relatively easy to assemble and reliable in operation.

It is a further object of this invention to provide such a valve which is electrically and magnetically efficient.

The present invention provides an electromagnetic valve comprising a housing having a fluid containing region and first and second ports in communication with the region, electromagnet means carried by the housing located external to the fluid containing region of the housing, and barrier means in the form of a thin diaphragm of fluid impermeable material which hermetically isolates the electromagnet from the fluid containing region. An armature is movably positioned in the region and has a pole portion located for magnetic attraction by the electromagnet means and has a plunger portion provided with valve means for opening and closing one of the ports to place both ports in fluid communication through the fluid containing region of the housing in one control state of the valve and to block fluid communication between the ports in another control state of the valve. The armature is moved from a rest position through a forward stroke when attracted by the electromagnet means to change the control state of the valve, and the armature is moved by biasing means in an opposite direction through a return stroke back to the rest position. The armature pole portion has a lateral dimension several times greater than the longitudinal dimension thereof and is of a material selected to achieve a desirable balance between fluid compatibility and magnetic properties for rapid and effective valve operation. Passage means in the barrier means and the armature pole portion allow for rapid valve movement and accommodate bubbles in the fluid, the armature is provided with means for effectively guiding the same and a valve seat structure resists fluid leaks. A magnetic circuit is defined including the electromagnet means, the armature pole portion, a portion of the barrier means and a gap between the pole portion and the electromagnet means located in the fluid containing region of the housing and external to the electromagnet means. The gap is closed in response to electrical energization the electromagnet means to move the armature and change the control state of the valve. The valve is made electrically and magnetically efficient by minimizing the total gap within the magnetic circuit, by having the pole face area relatively large on the armature pole portion and by having the electromagnet include a coil on a core of relatively small diameter.

The foregoing and additional advantages and characterizing features of the present invention will become clearly apparent upon a reading of the ensuing detailed description together with the included drawing wherein:

DETAILED DESCRIPTION OF THE ILLUSTRATED EMBODIMENT

Figure 1:
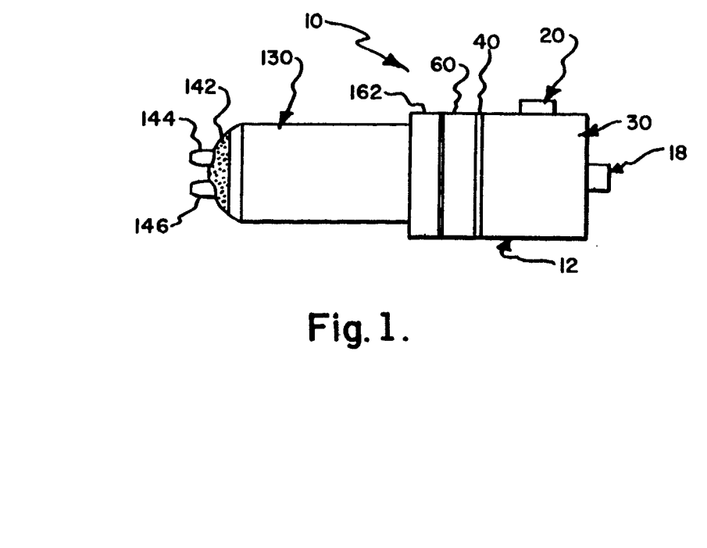
FIG. 1 is a side elevational view of a valve according to the present invention.
Figure 2:
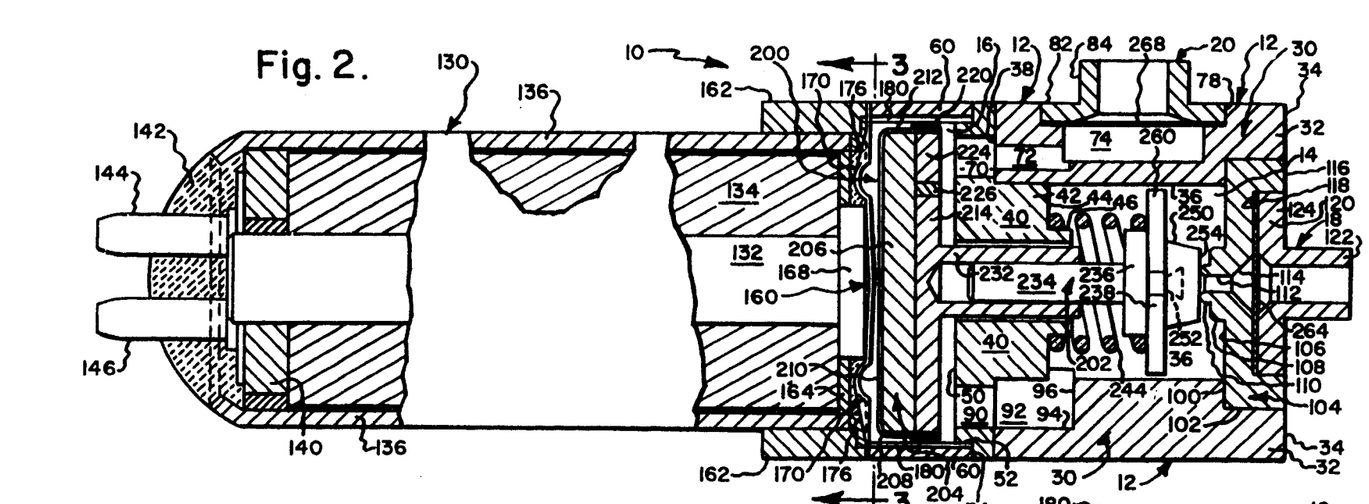
FIG. 2 is an enlarged longitudinal sectional view, partly in elevation, of the valve of FIG. 1 and illustrating one embodiment of the present invention.
Figure 3:
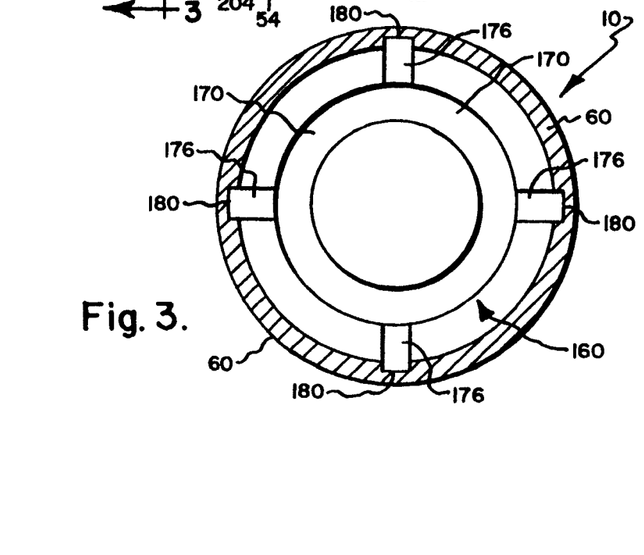
FIG. 3 is a sectional view taken about on line 3—3 in FIG. 2.

Referring now to FIGS. 1–3, a valve 10 according to one embodiment of the present invention includes a housing 12 which is generally hollow, either rectangular or cylindrical in overall shape, and valve 10 includes an interior region for containing fluid, i.e. the liquid to be delivered. As shown in FIG. 2 the hollow interior region is divided in a manner which will be described into a first chamber 14 and a second chamber 16 in fluid communication therewith. There is a first port generally designated 18 in fluid communication with the first chamber and adapted to be connected in the fluid handling circuit. There is also a second port 20 in fluid communication with the second chamber 16 and adapted to be connected in the fluid handling circuit. In the illustrative valve shown, port 20 is connected to the relatively higher pressure portion of the circuit, and port 18 is connected to the relatively lower pressure portion. Thus, port 20 may be viewed as the valve inlet and port 18 as the valve outlet. By way of example, in an illustrative implanted drug delivery system incorporating valve 10, the inlet and outlet 20 and 18, respectively, would be connected in a fluid circuit between a drug supply or reservoir and an outlet catheter for delivering the drug to the body site.

As shown in FIG. 2, housing 12 is generally hollow including a body portion 30 of relatively substantial wall thickness. Housing 12 also includes a first axial end portion 32 extending from one end of body 30, i.e. the right-hand end as viewed in FIG. 2, and which is of relatively smaller wall thickness terminating in an axial end face 34. Housing portion 30 defines an interior region of constant diameter having an inner surface 36. The housing portion 30 terminates at the other end thereof, i.e. the left-hand end as viewed in FIG. 2, in an end face 38.

Housing 12 further comprises a spring retainer element 40 in the form generally of a bushing having outer dimensions substantially equal to the outer dimensions of body portion 30 so as to be substantially flush therewith. Element 40 includes an axial extension 42 having an outer diameter substantially equal to the inner diameter of the body portion 30 so as to be received therein in a tight friction-like fit. Extension 42 terminates in an annular shoulder defined by axial and cylindrical surfaces 44 and 46, respectively, for providing a spring retaining function in a manner which will be described. The opposite end of element 40 terminates in an axial end face 50. An annular shoulder is defined by cylindrical and axial surfaces 52 and 54, respectively, at the peripheral junction between end face 50 and the outer surface of body 30. The shoulder receives one end of a first weld ring element 60 having an outer diameter substantially equal to the outer dimensions of element 40 so as to be substantially flush therewith. Ring element 60 is welded at the one end thereof, i.e. the right-hand end as viewed in FIG. 2, to element 40 at the aforementioned shoulder thereof in a suitable manner. Ring 60 is joined at the opposite end thereof to other components of the pump housing in a manner which will be described.

Chamber 16 is placed in fluid communication with port 20 in the following manner. A first longitudinal bore or passage 70 is provided in the body of retainer element 40, extending axially inwardly from end face 50, and a second longitudinal bore or passage 72 is provided in housing body portion 30 located so as to be open at one end to passage 70 and to be near port 20 at the other end thereof. A generally cylindrical chamber 74 is provided in housing body portion 30 in registry with port 20 and located so that the other end of passage 72 opens into the annular or circumferential wall of chamber 74. The one axial end of chamber 74 is defined by an internal surface in body portion 30. The opposite axial end of chamber 74 is open to port 20 and is circumscribed by an annular recess defining a ledge 78 which engages an annular rim 82 of a tubular fitting 84 which defines port 20. In the arrangement shown, the longitudinal axes of chamber 74 and fitting 84 are substantially coincident. The fitting 84 defining port 20 is adapted for connection to a conduit such as a flexible tubing comprising a portion of the afore-mentioned fluid circuit.

Thus, chamber 16 is placed in fluid communication with port 20 via the arrangement of passages 70 and 72 and chamber 74. Chamber 16 is placed in fluid communication with chamber 14 in the following manner. Another longitudinal bore or passage 90 is provided in the body of retainer element 40, extending axially inwardly from end face 50 and located substantially diametrically opposite the passage 70. Body portion 30 is provided with a recess 92 in the lower portion of the wall thereof as viewed in FIG. 2 and located so as to be in fluid communication with passage 90. Recess 92 is defined by an axially extending surface 94 and a radially extending surface 96 leading from surface 92 to the inner wall surface of body portion 30. As a result, the interior of body portion 30, and thus chamber 14, is placed in fluid communication with chamber 16 via the arrangement of passage 90 and recess 92.

Port 20 is provided by the following arrangement. A cylindrical recess of short axial length is provided in housing axial end face 34 and terminates in an inner annular end face 100. The inner surface 102 of the recess has a diameter larger than that of housing inner surface 36. Surfaces 100 and 102 define an annular shoulder which receives the cylindrical body of a ferrule element 104 in a tight-fitting relationship. Ferrule 104 has an inner axial end face 106 exposed to the housing interior region and is provided with a central, boss-like axial extension 108 having an axial end face provided with an annular valve seat formation 110 which is shaped to define a sharp annular edge facing axially into the housing interior region. A central bore or passage 112 of constant diameter extends axially inwardly from valve seat formation 110 whereupon it meets a passage 114 of increasing diameter. Ferrule 104 also has an outer axial end face 116 which meets housing end face 34 in a substantially flush relationship. A cylindrical recess 118 is formed in end face 116 and extends inwardly for about half the axial length of ferrule 104. A fitting 120 having a cylindrical portion 122 and an annular flange or lip 124 is received in recess 118. In particular, the outer diameter of lip 124 is substantially equal to the diameter of recess 118 to provide a tight fit. The axial length of lip 124 is substantially equal to the axial length of recess 118 so that the outer annular surface of lip 124 is substantially finish with ferrule end face 116. Thus, a flow path is defined through the central passage of fitting 120 and the passage portions 112 and 114.

By way of example, in an illustrative valve, housing 12 and the port fittings 84 and 120 all are of metal, and for a drug delivery valve for implantation in a patient, titanium has been formed to provide satisfactory results. In such an illustrative valve, housing 12 has an overall length of 0.36 inch measured between the axial end face 34 of body portion 30 and the outer axial end face of weld ring element 60. The inner surface 36 of housing body portion 30 has a diameter of 0.17 inch, and body portion 30 has an outer dimension of 0.31 inch. Passages 70 and 72 have diameters of 0.038 inch and 0.020 inch, respectively. Chamber 74 has an inner diameter of 0.12 inch and an axial length of 0.031 inch, and fitting 84 has an inner diameter of 0.062 inch. Passage 90 has a diameter of 0.038 inch. Passage 112 has a diameter of 0.015 inch, passage 114 has a maximum diameter of 0.055 inch, and fitting 120 has an inner diameter of 0.032 inch.

The valve of the present invention further comprises electromagnet means generally designated 130 carried by housing 12 and located external to the fluid containing region of the housing. As shown in FIG. 2 the electromagnet 130 includes a core 132 in the form of a spool which is generally solid cylindrical in shape. A coil 134 is wound on spool 132 and contained within a hollow housing 136 generally cylindrical in shape. One end of electromagnet 130 is adjacent and in abutting relation to housing 12 and the opposite end, i.e. the left-hand end as viewed in FIG. 2 is closed by an arrangement including a washer 140 and a body 142 of encapsulant such as expoxy material. A pair of terminals 144,146 provide electrical connection from a power source, such as a lithium battery charging circuit and capacitor, to electromagnet 130. Electromagnet 130 is joined to housing 12 in the following manner.

The interior, fluid containing region of housing 12 and the electromagnet 130 are separated by a barrier means of fluid impervious material in the form of a relatively thin plate or diaphragm-like component 160. A second weld ring 162 is provided on the end of magnet housing 136 adjacent housing 12. The outer diameter of ring 162 is substantially equal to the outer diameter of the first weld ring 60 so that the respective outer surfaces are substantially flush. The region between coil 134 and barrier 162 is filled with epoxy or like material generally designated 164. The housing and electromagnet structures are placed in abutting relation on opposite sides of the plate 160, and the assembly is secured together by a weld joining the respective outer surfaces of the weld rings 60 and 162. In addition, an enlarged annular end portion 168 of spool 132 contacts the central portion of plate 160 in a manner supporting the same. In accordance with the present invention, the central portion of barrier means or plate 160 is shaped in a manner to improve the operation of valve 10 during closing thereof in a manner which will be described. Plate 160 is formed with an annular groove or depression 170 in the surface facing housing 12 and having an inner diameter substantially equal to the outer diameter of spool end 168 to receive end 168 therein and strengthen plate 160.

In accordance with the present invention, barrier 160 also is formed with passage means generally designated 176 along the surface facing housing 12 for a purpose to be described. According to a preferred mode of the present invention as illustrated in FIG. 3, barrier means 160 is provided with four passage means or channels 176 at 90 degree angular increments around the circumference of barrier 160. Each passage means or channel 176 extends in a radial direction between groove 170 and the periphery of barrier plate 160. There is also provided, in accordance with the present invention, longitudinally extending passage means 180 formed in the housing inner surface for co-operating with the passage means 176 on the barrier means 160. In particular, the longitudinally extending passage means 180 are provided along the inner surface of weld ring 60, and as shown in FIG. 3. There are four passages 180 in circumferential registry or alignment with the channels 176. The role of the channels 176 and passages 180 in the operation of valve 10 will be described in detail presently.

By way of example, in an illustrative valve, spool 132, magnet housing 136 and washer 140 are of ferromagnetic material, preferably 4750 nickel iron alloy. Plate 160 and weld rings 60 and 162 are of titanium. Spool 132 has a length of about 0.56 inch and a diameter of about 0.10 inch. Housing 136 has a wall thickness of about 0.015 inch, rings 60 and 162 have thicknesses of about 0.016 inch and 0.024 inch, respectively, and diaphragm 160 has a thickness of about 0.001 inch. Coil 134 comprises about 4580 turns of 43 gauge wire.

The valve according to the present invention further comprises an armature generally designated 200 positioned in the fluid containing region of housing 12. The armature has a pole portion located for magnetic attraction by the electromagnet 130, a plunger portion in the chamber 16 and a valve portion for opening and closing port 18. The armature 200 is movably supported in housing 12 for movement from a rest position through a forward stroke when attracted by the electromagnet 130 to open port 18 to place the ports 18 and 20 in fluid communication through the chambers 14, 16 and for movement in an opposite direction through a return stroke back to the rest position closing port 18 and blocking fluid communication between ports 18,20 through chambers 14,16. In FIG. 2, armature 200 is shown in the rest position at the end of the return stroke.

Armature 200 includes a shaft or rod portion 202 which is positioned in housing 12 with the longitudinal axis thereof generally coincident with the longitudinal axis of housing 12. A major portion of the length is a section of relatively small diameter. Armature 200 includes a pole portion generally designated 204 which occupies a major portion of chamber 16 in which it is located, and pole portion 204 has a lateral dimension as viewed in FIG. 2 which is several times greater than the longitudinal dimension thereof. In accordance with the present invention, pole portion 204 comprises a body of magnetic material within a titanium enclosure, the encapsulation provided by the titanium enclosure providing protection against corrosion from insulin stabilized for use in implantable delivery systems and other corrosive drugs. In particular, pole portion 204 comprises a body 206 in the form of a disc. The enclosure comprises a thin-walled cap 208 having a base 210 contacting one axial face of disc 206 and an annular rim 212 contacting the periphery of disc 206. The enclosure is completed by a disc-shaped body 214 contacting the opposite axial end face of disc 206 and abutting the rim 212 of cap 208. As shown in FIG. 2, rim 212 of cap 208 extends slightly axially beyond the periphery of disc 206, body 214 fits within and contacts rim 212 and a weld ring 220 embraces the periphery of rim 212 so that ring 220, rim 212 and the disc-shaped body 214 can be welded together at the junctions thereof.

The disc-shaped body 214 is provided with at least one vent passage 224 therein to evacuate residual gas during assembly, the passage 224 being sealed by a plug 226 after assembly. Passage 224 is in the form of an axially extending through bore in body 214. The provisions of passage 224 and plug 226 is necessary because the small residual volume of gas within cup 208 must be evacuated to hold cup 208 tight against disc 206 even when the interior of valve 10 is at low pressure. Plug 226 is in the form of a filler pin and is welded in place with the entire assembly under vacuum to close the vent hole 224 in body 214.

By way of example, in an illustrative valve, disc 206 has a diameter of about 0.27 inch, an axial length of about 0.035 inch and is of 4750 nickel-iron alloy, body 214 has a diameter of about 0.27 inch, an axial length of about 0.14 inch and is of titanium, and cap 208 has a wall thickness of about 0.001 inch and is of titanium. The 4750 nickel-iron alloy has a relatively high saturation flux density. Weld ring 220 has a thickness of about 0.005 inch and is of titanium. Weld ring 220 facilitates welding the thin material of cup 208 by sandwiching it between ring 220 and disc-shaped body 214 and then making a laser weld.

Thus, the armature pole portion 204 terminates at the end facing electromagnet 130 in an axial end face which serves as the pole face and is disposed substantially perpendicular to the armature axis. The armature pole face together with electromagnet 130 define the magnetic circuit gap which is closed during the forward armature stroke. The pole face is of relatively large cross-sectional area as compared to the cross sectional area of the armature shaft portion 202. The armature pole portion 204 serves as the plunger portion of the armature, and as the pole face moves toward plate 160 when magnet 130 is energized, pole portion 204 upon moving in chamber 16 displaces fluid and moves it toward chamber 14.

Armature shaft portion 202 is joined to the pole portion 204 via a sleeve-like axial projection or bushing 232 extending from disc-shaped body 214 to which is attached an armature rod or shaft 234. The outer diameter of bushing 232 is slightly smaller than the inner diameter of retainer element 40 so that bushing 232 is freely longitudinally movable along within retainer 40. The attachment is made by crimping the bushing 232 which allows the length of the plunger assembly to be changed to adjust the plunger stroke. Shaft 234 is provided with an enlargement at the end opposite bushing 232 which includes two relatively larger diameter shaft sections. In particular, there is a first section 236 facing bushing 232 and a second, axially adjacent section 238 which is of larger diameter. The two sections are of relatively short axial length and they define therebetween a shoulder facing pole portion 204.

There is provided biasing means in the form of a coil spring 244 for urging armature 200 toward the rest position shown in FIG. 2. One end of spring 244 seats in the annular shoulder defined by the armature shaft sections 236,238. The opposite end of spring 244 seats in the annular shoulder defined by surfaces 44,46 of retainer element 40 previously described. Retainer 40 is concentric with the armature shaft portion 202 and receives spring 244 which also is concentric with armature shaft portion 202. As previously described, the armature shaft portion 202, in particular bushing 232, is freely axially movable within retainer 40.

Armature 200 has a valve portion at the axial end of the armature opposite that of the pole face portion 204 for closing the port 18 when the armature is in the rest position and for opening port 18 when the armature is moved during the forward pumping stroke. There is provided a valve element 250 in the form of a body of elastomer material having a frustoconical shape with the larger diameter axial end face thereof abutting the outer axial end face of armature shaft section 238. Element 250 is secured to shaft section 238 by a fastener in the form of a conical key designated 252. Element 250 has an outer flat axial end face 254 adapted to sealing contact the annular valve seat formation 110 in the closed condition or state of the valve as shown in FIG. 2. Element 250 preferably is of silicone rubber which provides a relatively soft valve seat more resistant to fluid leaks.

By way of example, in an illustrative valve, the armature rod or shaft 234 and the enlargement defined by the two sections 236,238 are machined from metal, preferably titanium. The overall length between the end of shaft 234 within bushing 232 to outer face of section 238 is about 0.17 inch. The outer diameter of shaft 234 is about 0.036 inch, the inner diameter of retainer 40 is about 0.073 inch and the axial length of bushing 232 is about 0.12 inch. Spring 244 is fabricated from a molybdenum chromium nickel cobalt alloy MP35N which is both corrosion resistant and suitable for spring fabrication. The outer diameter of end face 254 of valve element 250 is about 0.027 inch, and the diameter of the circular edge of formation 110 is about 0.027 inch. The outer diameter of shaft section 238 is about 0.168 inch.

The surfaces which guide the longitudinal movement of armature 200 are the pole button weld ring 220 and the annular flange 238. Flange 238 is provided with four flats at 90 degree intervals around the circumference thereof, two of which are designated and 262 260 in FIG. 2, to allow passage of the fluid flow past flange 238. Ports 18 and 20 are provided with filters 264 and 268, respectively, to protect against leaks caused by foreign particles which might otherwise enter valve 10. Filters 264, 268 preferably are of the etched titanium type.

In operation, port 18 is connected to an appropriate location in the relatively lower pressure portion of a fluid circuit, and port 20 is connected to a location in the higher pressure portion of the circuit. The armature 200 is moved through the forward stroke in response to electrical energization of the electromagnet 130. One way of energizing magnet 130 is to charge a capacitor from a battery and then discharge that capacitor through coil 134. Other procedures can of course be employed for electrically energizing coil 134 in a known manner. Prior to electrical energization of magnet 130, armature 200 is in the rest position of FIG. 2 where the valve body 250 at the end of armature 200 is firmly seated against the valve seat formation 110 to block fluid communication between port 18 and chamber 14. The end face 254 of body 250 is held firmly and sealingly against the edge of formation 110 by the force of biasing spring 244. In the rest position of armature 200, the pole face of portion 204 is spaced from barrier plate 160 as shown in FIG. 2 thereby defining the gap in the magnetic circuit. In the rest position this gap between the pole face and diaphragm 160 is of maximum length.

When coil 134 is energized, the armature pole portion 240 is attracted toward electromagnet 130 thereby causing armature 200 to be pulled toward diaphragm 160. Electromagnetic flux travels through the magnetic circuit including core 132, washer 140, magnet housing 136, weld ring 162, the included portion of the periphery of diaphragm 160 between weld rings 162 and 60, weld ring 60, armature pole body 206, and the gap between the armature pole face and diaphragm 160. As armature 200 is moved in the forward stroke, i.e. in a direct to the left as viewed in FIG. 2, the armature pole portion 204 moves further into chamber 16, the armature pole face moves closer to diaphragm 160 thereby decreasing the gap in the magnetic circuit, and the end face 254 of valve element 250 becomes unseated from the annular valve seat formation 110 thereby placing port 18, chambers 14, 16 and port 20 in fluid communication. Fluid thus flows from the relatively higher pressure port 20 through chamber 74 and through passages 72 and 70 into chamber 16, from chamber 16 through passage 90 and recess 92 into chamber 14 and from chamber 14 out through port 18. The forward stroke of armature 200 is against the biasing force of spring 244 and is completed when the pole face thereof approaches contact with diaphragm 160. During the foregoing mode of operation, movement of armature 200 is guided by flange 238 and weld ring 220 relative to the corresponding inner surface portions of the valve housing.

When electrical excitation of coil 134 ceases, armature 200 is moved in the opposite direction, i.e. to the right as viewed in FIG. 2, by the force of biasing spring 244 until the armature reaches the rest position as shown in FIG. 2 with end face 254 of valve element 250 firmly seated on formation 110. Armature 200 then remains in the rest position of FIG. 2 closing port 18 and waiting for the next forward stroke which occurs when magnet 130 is energized again. In the illustrative mode where the coil 134 is excited by the discharge of a capacitor therethrough, the time during which valve 10 places ports 18 and 20 in communication, i.e. the time during which valve 10 is open, is relatively short. However, having the valve open for such a relatively short time is called for in typical implantable drug dosage delivery systems. Alternatively, valve 10 can be held open for whatever longer duration may be desired simply by continuing the energization of magnet 130. In the foregoing mode of operation, when armature 200 initially begins movement toward the rest position for closure of valve 10, the passage means or channels 176 in barrier 160 serve to shorten the time required for the armature pole 204 to separate from barrier 160 at the outset of armature movement. The passage means or channels 176 also serve to reduce the possibility that the effects of surface tension, if some air should be present within the valve, might cause valve 10 to remain open after electromagnet 130 is no longer energized. In addition, as shown in FIG. 2, the central portion of barrier 160 radially inwardly of annular groove 170 is provided with a slightly conical shape with the apex or tip of the cone pointing toward or facing armature 200. The cone thus defined is very blunt and nearly flat, the angle of the cone measured relative to the longitudinal axis of valve 10 being approximately 89°. The taper of this conical central portion of barrier 160 is sufficient to change the behavior of the armature 200 during closing of valve 10 as compared to a completely flat or planar central portion of barrier 160. In particular, the conical central portion of barrier 160 is believed to prevent the formation of a gas-liquid interface encircling the armature pole face surface 210 in contact with barrier plate 160 which gas-liquid interface could support a pressure difference at the armature pole face sufficient to overcome the force of armature return spring thereby slowing or interfering with closing of valve 10.

The non-movable diaphragm 160 of titanium or like material provides an hermetic seal between the fluid in housing 12 and the electrical components associated with electromagnet 130. Having armature 200 immersed in the fluid makes operation of the valve nearly independent of ambient pressure. The initial condition of the valve 10 when armature 200 is in the rest position of FIG. 2 is that fluid is at substantially the same pressure on opposite sides of the armature pole portion 204, i.e. in the two chambers 14 and 16.

The valve 10 of the present invention is made electrically and magnetically efficient by minimizing the total gap within the magnetic circuit, by having the magnetic pole face of armature pole portion 204 of relatively large surface area, and by having core 132 of relatively small cross-sectional area. In particular, there is a relatively large contact area at the interface between the axial end face of weld ring 162 and diaphragm 160 and between diaphragm 160 and the axial end face of weld ring 60 to minimize the effective air gap introduced by diaphragm 160 at this point in the magnetic circuit. In other words, diaphragm 160 is relatively thin in relation to the afore-mentioned contact area. Related to this is the need for welding diaphragm 160 to rings 60 and 162 to achieve an hermetic seal between electromagnet 130 and the fluid containing region of housing 12 while at the same time not adversely affecting the magnetic circuit. In addition, there is a relatively large surface area in relation to the gap or space between weld ring 60 and the periphery of armature pole portion 204 to minimize the effective air gap introduced at this point in the magnetic circuit. The relatively small diameter of core 132 provides the necessary number of ampere turns with a minimum electrical resistance. The large area of the pole face of the disc-shaped armature pole portion 204 provides a high magnetic force with a minimum number of ampere turns. Having the magnetic gap external to coil 134, i.e. between the armature pole face and diaphragm 160, allows the foregoing features to be achieved simultaneously.

The valve 10 of the present invention is small in size having an overall outer dimension of about 0.31 inch and an over-all length of about 0.96 inch, and has the relatively light weight of about 5.2 grams. A valve of the present invention as described hereinabove can be opened with an initial power drain of as little as 70 milliwatts and held open with 20 milliwatts power drain thereby operating at exceptionally low power levels.

Figure 4:
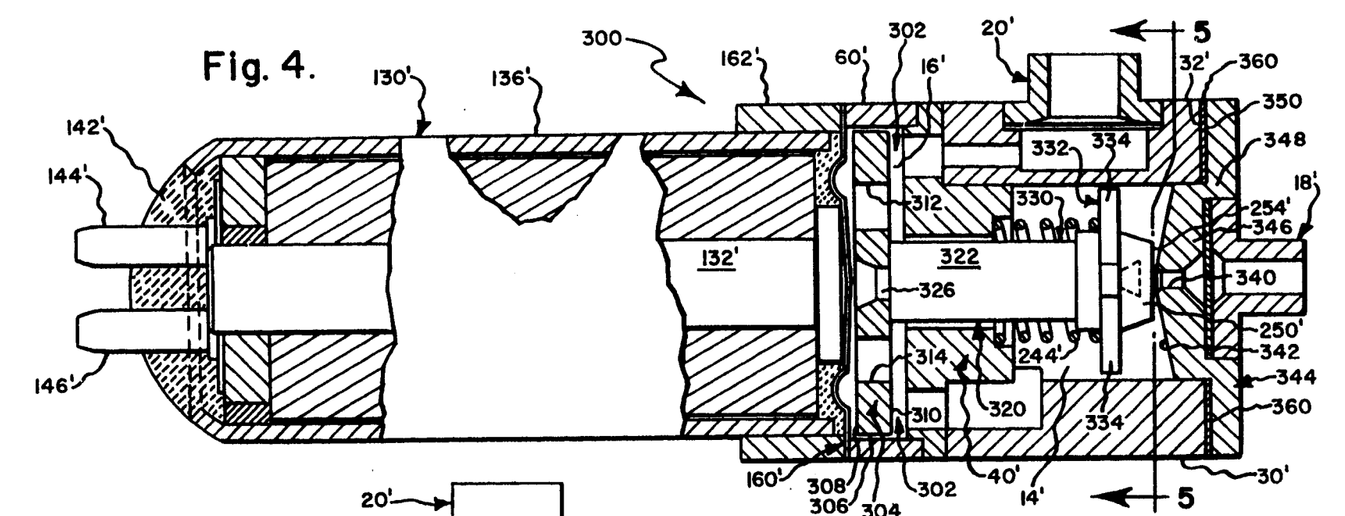
FIG. 4 is a view similar to FIG. 2 illustrating a valve according to another embodiment of the present invention.
Figure 5:
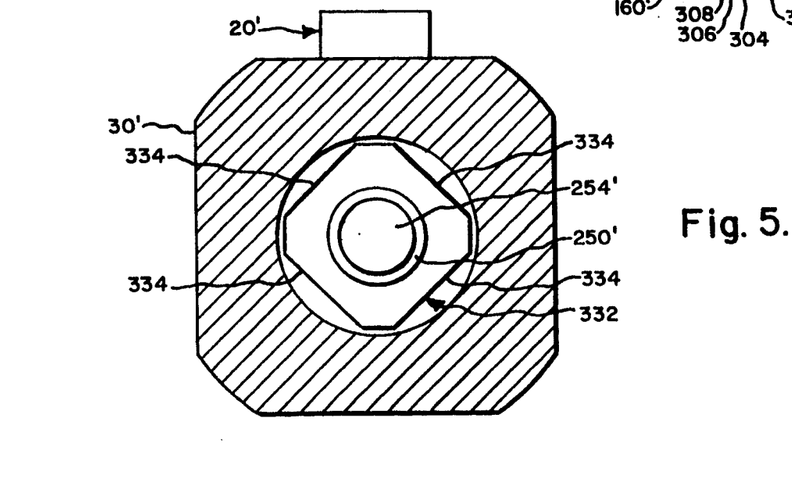
FIG. 5 is a sectional view taken about on line 5—5 in FIG. 4.

FIGS. 4 and 5 show a valve 300 according to another embodiment of the present invention. Components of valve 300 similar to those of valve 10 are identified by the same reference numeral with a prime designation. A principal difference between the two embodiments is that armature 302 in valve 300 is simpler in structure and relatively easier to manufacture and assemble. In particular armature 302 has a pole portion 304 comprising a solid, monolithic body having the shape or form of a disc. The circumferential surface 306 of pole portion 304 is located relatively close to the inner surface of weld ring 60' so that armature pole portion 304 occupies a major portion of the volume of chamber 16'. The lateral dimension of pole portion 304 is several times the longitudinal dimension thereof. Pole portion 304 has a first axial end face 308 which faces toward barrier means 160' and a second, opposite axial end face 310 which faces toward port 18'. Thus, end faces 308,310 are disposed substantially perpendicular to the direction of travel of armature 302.

Pole portion 304 is exclusively of magnetic material, preferably a chrome-molybdenum-iron alloy which is heat treated. Examples are 29-4 and 29-4C chrome-molybdenum iron alloy. This alloy has high corrosion resistance, and has adequate magnetic characteristics for use in valve 300 when heat treated. In other words, the alloy is heat treated to provide a BH characteristic for the alloy which yields the requisite level of magnetic flux density and coercive force. Furthermore, the alloy is sufficiently resistant to corrosive effects of insulin stabilized for use in implantable drug delivery systems as well as other corrosive drugs.

In particular, the afore-mentioned chrome-molybdenum-iron alloy is a ferritic stainless steel alloy containing 29% chromium, 4% molybdenum and the remainder substantially iron. The afore-mentioned heat treatment involves an anneal and rapid cool of the armature pole portions 302. In particular the procedure involves a short magnetic anneal at a temperature above that which can form a harmful second phase in the alloy followed by cooling rapidly enough to avoid second phase formation but not so rapidly as to degrade magnetic properties. Heating of armature pole buttons 302 of 29-4 alloy is performed for example in a clamshell furnace at a temperature of about 1010° C. for about twenty minutes whereupon the parts 302 are removed quickly to the ambient in a manner allowing complete cooling for a minimum of 25 minutes. The cooling rate during the first portion of the cooling cycle from 1010° C. down to black, i.e. down to 600° C., should be maintained at about 60 seconds.

The armature body 304 is provided with at least one passage means therethrough, and in the valve shown two axially extending through bores or passages 312,314 are shown. The passages 312,314 extend through the entire axial length of armature body 304 between the axial end faces 308,310. Passage means 312,314 serve to reduce the time required for armature pole portion 304 to separate from barrier means 160' during movement of armature 302 toward port 18' and to reduce surface tension effects between barrier means 106' and pole portion 304. The path for fluid flow defined by passage means 312,314 provides the foregoing results when energization of electromagnet 130' ceases and the force of spring 244' begins to move armature pole portion 304 away from barrier means 106'. In addition, barrier 160' is provided with a central conical formation identical to that of barrier 160 in the embodiment of FIG. 2 and which functions in an identical manner for the same purpose.

Thus, the one-piece pole portion 304 of armature 302 contributes to the simplicity in structure and ease of manufacture and assembly. These advantages also result from the provision of an armature shaft portion 320 which simply is fastened at one end to the pole portion 304. In particular, armature shaft portion 320 includes a rod-like body 322 having an axial end face 324 which buts the axial end face 310 of pole portion 304. A rivet 326 or similar fastening means is employed to simply attach shaft portion 320 to pole portion 304. The outer diameter of rod 322 is slightly smaller than the inner diameter of spring retainer 40'. As in the previous embodiment, rod 322 is provided with an enlargement at the opposite end which includes two relatively larger diameter sections. In particular, there is a first section 330 which faces pole portion 304 and a second, axially adjacent section 332 which is of larger diameter, the two sections being of relatively short axial length and defining a shoulder therebetween facing pole portion 304 for receiving one end of biasing spring 244'. As in the previous embodiment, section 332 serves as a guiding flange to provide one of she surfaces which guides the longitudinal movement of armature 300. Flange 332 is provided with four flats 334 at 90 degree intervals around the circumference thereof, as shown in FIG. 5, to allow passage of the fluid past flange 332. The other armature guiding surface is the peripheral surface 306 of armature pole portion 304.

Armature 302 has a valve portion at the axial end thereof opposite pole portion 304 which valve portion is identical to valve element 250' of the previous embodiment. In this embodiment, the valve seat formation which is sealingly contacted by end face 254' of valve element 250' is defined by the annular edge or junction between the central opening or passage 340 and the conical end face 342 of ferrule element 344 which closes the one axial end of housing 12', i.e. the right-hand end as viewed in FIG. 4. In particular, conical end face 342 is formed on the end of a central body portion 346 of ferrule 344 which fits snugly in the housing inner surface 36'. Ferrule 344 has an annular body portion 348 which has an inner axial end face 350 which meets the axial end portion 32' of housing 36' and an outer axial end face 352. The outer diameter of body portion 348 is substantially equal to the outer diameter of housing 30' so that the respective outer surfaces are substantially flush. The conical surface 342 is of simple constructions yet provides an effective valve seat formation. Plunger stroke adjustment is provided by shims 360 which are placed between housing end portion 32' and end face 350 of ferrule 344.

By way of example, in an illustrative valve, pole portion 304 has an outer diameter of about 0.264 inch and an axial length of about 0.036 inch, passages 312,314 each have a diameter of about 0.040 inch, rod 322 has an axial length of about 0.16 inch and a diameter of about 0.07 inch, conical surface 342 defines an angle of about 10 degrees with a plane perpendicular to the longitudinal axis of armature 300 and passage 340 has a diameter of about 0.015 inch.

It is therefore apparent that the present invention accomplishes its intended objects. While embodiments of the present invention have been described in detail, that is for the purpose of illustration, not limitation.

What is claimed is:

1. A low power electromagnetic valve for use with implantable fluid delivery systems, said valve comprising:
    a) a housing including a fluid containing region having first and second chambers and first and second ports in fluid communication with said first and second chambers, respectively;
    b) electromagnet means carried by said housing and located externally of said fluid containing region;
    c) barrier means of fluid-impervious material for isolating said electromagnet means from said fluid containing region of said housing;
    d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;
    e) said armature pole portion comprising a solid body exclusively of corrosion resistant magnetic material occupying a major portion of the one of said chambers in which it is located and having a lateral dimensions several times greater than the longitudinal dimensions thereof, said magnetic material consisting essentially of a heat treated alloy of chrome, molybdenum and iron; and
    f) means for defining a magnetic circuit including said electromagnet, said armature pole portion, a portion of said barrier means and a gap between said pole portion and said electromagnet means located in said fluid containing region of said housing and external to said electromagnet means for closing said gap in response to electrical energization of said electromagnet to move said armature and change the control state of said valve.

2. A valve according to claim 1, wherein said armature pole portion contacts a surface of said barrier means when said gap is closed to change the control state of said valve and wherein said pole portion is provided with passage means through the body thereof to reduce the time required for said pole portion to separate from said barrier means during movement of said armature and to reduce surface tension effects between said barrier means and said pole portion.

3. A valve according to claim 1, wherein said armature pole portion and said plunger portion are of fixed length and wherein said one port is located in a component of said housing separated from the remainder of said housing by shim means so as to allow adjustment of the distance between said one port and said valve means on said plunger portion.

4. A valve according to claim 1, wherein said valve means comprises a valve seat carried by said plunger and having a surface disposed substantially perpendicular to the direction of travel of said armature and wherein said one port is defined on an inner surface of said housing having a frusto conical formation diverging away from said valve seat surface to facilitate initial fluid flow upon opening of said valve.

5. A valve according to claim 1, wherein said armature plunger portion is provided with guiding means in the form of a flange disposed substantially perpendicular to the direction of armature travel and having a peripheral surface in closely spaced relation to the inner surface of said housing.

6. A valve according to claim 5, further including at least one flow passage means formed in said peripheral surface of said flange.

7. A valve according to claim 1, wherein said housing is elongated having a longitudinal axis, said armature being positioned for movement along said housing longitudinal axis, and wherein said fluid containing region of said housing and said electromagnet means are in axially spaced relation along said housing longitudinal axis.

8. A valve according to claim 1, wherein said armature pole portion is formed of an alloy of chrome, molybdenum and iron and then subjected to magnetic annealing for a relatively short time at a temperature above that which can form a harmful second phase in the alloy followed by cooling at a rate rapid enough to avoid second phase formation but not so rapid as to degrade the magnetic properties of the alloy.

9. A low power electromagnetic valve for use with implantable fluid delivery systems, said valve comprising:
   a) a housing including a fluid containing region having first and second chambers and first and second pores in fluid communication with said first and second chambers, respectively;
   b) electromagnet means carried by said housing and located externally of said fluid containing region;
   c) barrier means of fluid-impervious material for isolating said electromagnet means from said fluid containing region of said housing;
   d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;
   e) said housing being elongated having a longitudinal axis, said armature being positioned for movement along said housing longitudinal axis, and said fluid containing region of said housing and said electromagnet means being in axially spaced relation along said housing longitudinal axis;
   f) said armature pole portion occupying a major portion of the one of said chambers in which it is located and having a lateral dimension several times greater than the longitudinal dimension thereof;
   g) said armature pole portion having a fluid-containing section of material which is compatible with the fluid delivered by said system;
   h) means for defining a magnetic circuit including said electromagnet, said armature pole portion, a portion of said barrier means and a gap between said pole portion and said electromagnet means located in said fluid containing region of said housing and external to said electromagnet means for closing said gap in response to electrical energization of said electromagnet to move said armature and change the control state of said valve; and
   i) said armature pole portion contacting said barrier means when said gap is closed to change the control state of said valve and said barrier means including a surface portion of conical shape wherein the apex of the cone faces toward said armature pole portion so as to enhance the separation of said pole portion from said barrier means during movement of said armature.

10. A low power electromagnetic valve for use with implantable fluid delivery systems, said valve comprising:
   a) a housing including a fluid containing region having first and second chambers and first and second ports in fluid communication with said first and second chambers, respectively;
   b) electromagnet means carried by said housing and located externally of said fluid containing region;
   c) barrier means of fluid-impervious material for isolating said electromagnet means from said fluid containing region of said housing;
   d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;
   e) said armature pole portion comprising a solid body exclusively of magnetic material occupying a major portion of the one of said chambers in which it is located and having a lateral dimension several times greater than the longitudinal dimensions thereof, said magnetic material consisting essential of a heat treated alloy of chrome, molybdenum and iron;

f) means for defining a magnetic circuit including said electromagnet, said armature pole portion, a portion of said barrier means and a gap between said pole portion of said electromagnet means located in said fluid containing region of said housing and external to said electromagnet means for closing said gap in response to electrical energization of said electromagnet to move said armature and change the control state of said valve; and g) said armature pole portion contacting said barrier means when said gap is closed to change the control state of said valve and said barrier means including a surface portion of conical shape wherein the apex of the cone faces toward said armature pole portion so as to enhance the separation of said pole portion from said barrier means during movement of said armature.

11. A low power electromagnetic valve for use with implantable fluid delivery systems, said valve comprising:

a) a housing including a fluid containing region having first and second chambers and first and second ports in fluid communication with said first and second chambers, respectively;

b) electromagnet means carried by said housing and located externally of said fluid containing region;

c) barrier means of fluid-impervious material for isolating said electromagnet means from said fluid containing region of said housing;

d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports no place said ports in fluid communication through said fluid containing region of said housing in one control state of said valve and to block fluid communication between said ports through said fluid containing region of said housing in another control state of said valve;

e) said housing being elongated having a longitudinal axis, said armature being positioned for movement along said housing longitudinal axis, and said fluid containing region of said housing and said electromagnet means being in axially spaced relation along said housing longitudinal axis;

f) said armature pole portion occupying a major portion of the one of said chambers in which it is located and having a lateral dimension several times greater than the longitudinal dimension thereof;

g) said armature pole portion having a fluid-contacting section of material which is compatible with and corrosion resistant to the fluid delivered by said system, said armature pole portion comprising a body of magnetic material within a titanium enclosure; and h) means for defining a magnetic circuit including said electromagnet, said armature pole portion, a portion of said barrier means and a gap between said pole portion and said electromagnet means located in said fluid containing region of said housing and external to said electromagnet means for closing said gap in response to electrical energization of said electromagnet to move said armature and change the control state of said valve.

12. A valve according to claim 11, wherein said body is in the form of a disc and wherein said enclosure comprises a cap having a base contacting one axial face of said disc and an annular rim contacting the periphery of said disc and a disc-shaped body contacting the opposite axial end face of said disc and abutting said rim of said cap.

13. A valve according to claim 12, wherein said rim of said cap extends slightly axially beyond the periphery of said disc and said disc-shaped body fits within and contacts said rim of said cap and further including a weld ring embracing the periphery of said rim so that said ring, rim and disc-shaped body can be welded together at the junctions thereof.

14. A valve according to claim 12, further including at least one vent passage provided in said disc shaped body to evacuate residual gas during assembly, said passage being sealed by a plug after assembly.

15. A valve according to claim 11, wherein said body is of nickel-iron alloy.

16. A valve according to claim 11, wherein said armature pole portion is in the shape of a disc wherein the opposite axial end faces of said disc are disposed substantially perpendicular to the direction of travel of said armature and wherein the periphery of said disc is located close to the inner surface of said housing.

17. A valve according to claim 11, further including filter means at said first and second ports.

18. A valve according to claim 11, wherein said valve means comprises a valve element associated with said one port and a valve seat carried by said plunger for contacting said valve element.

19. A valve according to claim 18, wherein said valve element comprises an annular body surrounding said one port and provided with a sharp annular edge axially facing toward said valve seat, and wherein said valve seat comprises a body of elastomer material on the end of said plunger having a flat axial surface adapted to sealingly contact said annular edge.

20. A valve according to claim 11, wherein said valve means comprises a valve seat carried by said plunger and having a surface disposed substantially perpendicular to the direction of travel of said armature and wherein said one port is defined on an inner surface of said housing having a frusto conical formation diverging away from said valve seat surface to facilitate initial fluid flow upon opening of said valve.

21. A low power electromagnetic valve for use with implantable fluid delivery systems, said valve comprising:

a) a housing including a fluid containing region having first and second chambers and first and second ports in fluid communication with said first and second chambers, respectively;

b) electromagnet means carried by said housing and located externally of said fluid containing region;

c) barrier means of fluid-impervious material for isolating said electromagnet means from said fluid containing region of said housing;

d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;

e) said housing being elongated having a longitudinal axis, said armature being positioned for movement along said housing longitudinal axis, and said fluid containing region of said housing and said electromagnet means being in axially spaced relation along said housing longitudinal axis;

f) said armature pole portion occupying a major portion of the one of said chambers in which it is located and having a lateral dimension several times greater than the longitudinal dimension thereof;

g) said armature pole portion having a fluid-contacting section of material which is compatible with and corrosion resistant to the fluid delivered by said system; and h) means for defining a magnetic circuit including said electromagnet, said armature pole portion, a portion of said barrier means and a gap between said pole portion and said electromagnet means located in said fluid containing region of said housing and external to said electromagnet means for closing said gap in response to electrical energization of said electromagnet to move said armature and change the control state of said valve;

i) said armature pole portion contacting a surface of said barrier means when said gap is closed to change the control state of said valve and said barrier means being provided with passage means along said surface to reduce the time required for said pole portion to separate from said barrier means during movement of said armature and to reduce surface tension effects between said barrier and said pole portion.

22. A valve according to claim 21, wherein said armature pole portion has a peripheral surface in closely spaced relation to the inner surface of said housing and further including longitudinally extending passage means formed in said peripheral surface for co-operating with said passage means on said barrier means.

23. A valve according to claim 21, wherein said armature pole portion has a peripheral surface in closely spaced relation to the inner surface of said housing and further including longitudinally extending passage means formed in said housing inner surface adjacent said pole portion peripheral surface for co-operating with said passage means on said barrier means.

24. A low power electromagnetic valve for use with implantable fluid delivery systems, said valve comprising:

a) a housing including a fluid containing region having first and second chambers and first and second pores in fluid communication with said first and second chambers, respectively;

b) electromagnet means carried by said housing and located externally of said fluid containing region;

c) barrier means of fluid-impervious material for isolating said electromagnet means from said fluid containing region of said housing;

d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;

e) said armature pole portion being provided with a longitudinally extending bushing and said armature plunger portion comprising a shaft received in said bushing so that the length of the plunger can be changed to adjust the stroke;

f) said housing being elongated having a longitudinal axis, said armature being positioned for movement along said housing longitudinal axis, and said fluid containing region of said housing and said electromagnet means being in axially spaced relation along said housing longitudinal axis;

g) said armature pole portion occupying a major portion of the one of said chambers in which it is located and having a lateral dimension several times greater than the longitudinal dimension thereof;

h) said armature pole portion having a fluid-contacting section of material which is compatible with and corrosion resistant to the fluid delivered by said system; and i) means for defining a magnetic circuit including said electromagnet, said armature pole portion; a portion of said barrier means and a gap between said pole portion and said electromagnet means located in said fluid containing region of said housing and external to said electromagnet means for closing said gap in response to electrical energization of said electromagnet to move said armature and change the control state of said valve.

25. A low power electromagnetic valve for use with implantable fluid delivery systems, said valve comprising:

a) a housing including a fluid containing region having first and second chambers and first and second ports in fluid communication with said first and second chambers, respectively;

b) electromagnet means carried by said housing and located externally of said fluid containing region;

c) barrier means of fluid-impervious material for isolating said electromagnet means from said fluid containing region of said housing;

d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;

e) said housing being elongated having a longitudinal axis, said armature being positioned for movement along said housing longitudinal axis, and said fluid containing region of said housing and said electromagnet means being in axially spaced relation along said housing longitudinal axis;

f) said armature pole portion occupying a major portion of the one of said chambers in which it is located and having a lateral dimension several times greater than the longitudinal dimension thereof;

g) said armature pole portion having a fluid-contacting section of material which is compatible with and corrosion resistant to the fluid delivered by said system;

h) means for defining a magnetic circuit including said electromagnet, said armature pole portion, a portion of said barrier means and a gap between said pole portion and said electromagnet means located in said fluid containing region of said housing and external to said electromagnet means for closing said gap in response to electrical energization of said electromagnet to move said armature and change the control state of said valve; and i) said armature plunger portion being provided with guiding means in the form of a flange disposed substantially perpendicular to the direction of armature travel and having a peripheral surface in closely spaced relation to the inner surface of said housing.

26. A valve according to claim 25, further including at least one flow passage means formed in said peripheral surface of said flange.

27. A low power electromagnetic valve for use with implantable fluid delivery systems, said valve comprising:

a) a housing including a fluid containing region having first and second chambers and first and second ports in fluid communication with said first and second chambers, respectively;

b) electromagnet means carried by said housing and located externally of said fluid containing region;

c) barrier means of fluid-impervious material for isolating said electromagnet means from said fluid containing region of said housing;

d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;

e) said housing being elongated having a longitudinal axis, said armature being positioned for movement along said housing longitudinal axis, and said fluid containing region of said housing and said electromagnet means being in axially spaced relation along said housing longitudinal axis;

f) said armature pole portion occupying a major portion of the one of said chambers in which it is located and having a lateral dimension several times greater than the longitudinal dimension thereof;

g) said armature pole portion having a fluid-contacting section of material which is compatible with and corrosion resistant to the fluid delivered by said system, said armature pole portion comprising a solid body of chrome-molybdenum-iron alloy heat treated to provide enhanced magnetic flux density and coercive force properties; and h) means for defining a magnetic circuit including said electromagnet, said armature pole portion, a portion of said barrier means and a gap between said pole portion and said electromagnet means located in said fluid containing region of said housing and external to said electromagnet means for closing said gap in response no electrical energization of said electromagnet to move said armature and change the control state of said valve.

28. A low power electromagnetic valve for use with implantable fluid delivery systems, said valve comprising:

a) a housing including a fluid containing region having first and second chambers and first and second ports in fluid communication with said first and second chambers, respectively;

b) electromagnet means carried by said housing and located externally of said fluid containing region;

c) barrier means of fluid-impervious material for isolating said electromagnet means from said fluid containing region of said housing;

d) an armature movably positioned in said fluid containing region of said housing and having a pole portion located in one of said first and second chambers for magnetic attraction by said electromagnet means and having a plunger portion provided with valve means located in the other of said first and second chambers for opening and closing one of said ports to place said ports in fluid communication through said fluid containing region of said housing in one control state of said valve and to block fluid communication between said ports through said fluid containing region of said housing in another control state of said valve;

e) said armature pole portion and said plunger portion being of fixed length and said one port being located in a component of said housing separated from the remainder of said housing by shim means so as to allow adjustment of the distance between said one port and said valve means on said plunger portion;

f) said housing being elongated having a longitudinal axis, said armature being positioned for movement along said housing longitudinal axis, and said fluid containing region of said housing and said electromagnet means being in axially spaced relation along said housing longitudinal axis;

g) said armature pole portion occupying a major portion of the one of said chambers in which it is located and having a lateral dimension several times greater than the longitudinal dimension thereof;

h) said armature pole portion having a fluid-contacting section of material which is compatible with and corrosion resistant to the fluid delivered by said system; and i) means for defining a magnetic circuit including said electromagnets said armature pole portion, a portion of said barrier means and a gap between said pole portion and said electromagnet means located in said fluid containing region of said housing and external to said electromagnet means for closing said gap in response to electrical energization of said electromagnet to move said armature and change the control state of said valve.

* * * * *

UNITED STATES PATENT AND TRADEMARK OFFICE
CERTIFICATE OF CORRECTION

PATENT NO.   : 5,368,274

DATED        : November 29, 1994

INVENTOR(S)  : Theodore J. Falk, Richard Brown, Lawrence E. Morris, Norbert W. Franz, Jr.

It is certified that error appears in the above-identified patent and that said Letters Patent is hereby corrected as shown below:

Title page, item [75],
    Change the name of the Inventor from "Franz" to --Frenz--.

Signed and Sealed this

Eighteenth Day of April, 1995

BRUCE LEHMAN

*Attest:*

*Attesting Officer*  *Commissioner of Patents and Trademarks*